United States Patent [19]
Bertling

[11] Patent Number: 6,165,772
[45] Date of Patent: Dec. 26, 2000

[54] VEHICLE FOR THE TRANSPORT OF MOLECULAR SUBSTANCES

[76] Inventor: Wolf Bertling, Meisenweg 22-91956, Erlangen, Germany

[21] Appl. No.: 09/155,786

[22] PCT Filed: May 7, 1997

[86] PCT No.: PCT/DE97/00919

§ 371 Date: Oct. 2, 1998

§ 102(e) Date: Oct. 2, 1998

[87] PCT Pub. No.: WO97/43431

PCT Pub. Date: Nov. 20, 1997

[30] Foreign Application Priority Data

May 10, 1996 [DE] Germany .............................. 196 18 787

[51] Int. Cl.$^7$ ....................................................... C12N 7/00
[52] U.S. Cl. ............................................ 435/235; 530/350
[58] Field of Search ..................................... 435/440, 456, 435/235, 320.1; 924/93.6; 530/350

[56] References Cited

U.S. PATENT DOCUMENTS 4,950,599  8/1990  Bertling .................................... 435/456

FOREIGN PATENT DOCUMENTS 2 268 492  1/1994  United Kingdom .

*Primary Examiner*—Remy Yucel
*Attorney, Agent, or Firm*—Vanophem Meehan & Vanophem, P.C.

[57] ABSTRACT

The invention relates to a vehicle for the transport of molecular substance, such as DNA, RNA, protein, PNA, pharmaceuticals of lipophilic and lipophobic character, into eukaryotic cells comprising at least one capsomere derived or originating from a virus, which on one of its sides interacts with the molecular substance such that the molecular substance can be bound or added to the capsomere.

15 Claims, 4 Drawing Sheets

VEHICLE FOR THE TRANSPORT OF MOLECULAR SUBSTANCES

BACKGROUND OF THE INVENTION

The invention relates to a vehicle for the transport of molecular substance, such as DNA, RNA, protein, PNA, pharmaceuticals of lipophilic and lipophobic character, into eukaryotic cells. The invention furthermore relates to a process for the preparation of the vehicle, its use and compositions of agents for applying or carrying out the invention.

Under certain conditions, eukaryotic cells absorb DNA, proteins and other molecules. The absorption rate, however, is usually low. Additionally, the transport of the molecular substance is not predeterminable with respect to the nature of the cells and the cell compartment or the site in the intracellular region.

In order to improve, in particular, the absorption of DNA into eukaryotic cells, it is known to use viral vectors as vehicles for transport into the cell. The use of viral vectors is disadvantageous because in this case the cotransfection of viral genomes can occur.

It is furthermore disclosed in U.S. Pat. No. 4,950,599 to lock molecular substance such as DNA into eukaryotic cells using empty virus capsids, in particular polyoma capsids. Even in this process cotransfection of viral genomes cannot be excluded. Additionally, molecules whose size exceed the internal volume of the polyoma capsid cannot be packed therein. Finally, synthetic preparation of polyoma capsids, which comes into consideration as one possibility of avoiding cotransfection, is extremely difficult and cost-intensive.

The object of the invention is to eliminate the disadvantages of the prior art, in particular to indicate a vehicle for the transport of molecular substance into eukaryotic cells which can be used universally and can be prepared simply and in a cost-effective manner.

This object is achieved by the features of claim 1. Advantageous embodiments of the invention are clear from the features of claims 2–15.

SUMMARY OF THE INVENTION

According to the invention, a vehicle is provided which contains at least one capsomere derived or originating from a virus, which on one of its sides has a structure interacting with the molecular substance such that the molecular substance can be bound or added to the capsomere.

The vehicle according to the invention has the advantage that it can be synthetically prepared relatively simply. Cotransfection of viral genomes can thus be avoided. Additionally, because of the provision of the structure interacting with the molecular substance, molecular substance of any size can be bound and locked into cells. To do this, the typical capsid form no longer has to be maintained. Using the vehicles according to the invention, besides capsomeres protective forms of a different kind are also formed. A particular advantage of the invention can be seen in that, with the vehicle according to the invention, depending on the formation of the at least one capsomere, it is possible to transport the molecular substance specifically into certain cells and/or to a prespecified site in the intracellular region.

The capsomere is preferably formed such that it is suitable for the construction of a capsid or a capsid-like structure. It is particularly advantageous if the capsomere spontaneously forms capsids.

According to a further embodying feature of the invention, the capsomere is derived from the polyoma virus, it being possible to form it from the VP1 pentamer of the polyoma virus.

Alternatively, the capsomere can be obtained from "non-enveloped" viruses such as DNA-containing Papovaviridae, in particular polyoma viruses and the papilloma viruses, Iridoviridae, Adenoviridae, Parvoviridae or RNA-containing Picornaviridae, in particular polio viruses, Caliciviridae, Reoviridae and Birnaviridae, or derived therefrom. Depending on the type of molecular substance to be transported, it may also be advantageous to obtain the capsomere from the outer and/or inner coat of "enveloped" viruses such as DNA-containing Poxviridae, Herpesviridae, Hepadnaviridae or RNA-containing Retroviridae, Paramyxoviridae, Sendai viruses, Orthomyxoviridae, Bunyaviridae, Arenaviridae, Toroviridae, Togaviridae, Flaviviridae, Rhabdoviridae and Filoviridae or to derive it therefrom.

The interactions are expediently lipophilic interactions and/or interactions which are based on covalent bonds, ionic bonds or hydrogen bridges. It is thus ensured that the molecular substance on transporting into the cell remains safely bound or adhered to the vehicle, but after transport into the cell has taken place is released from the vehicle or can be detached by cellular systems.

The structure can comprise bifunctional, preferably heterologous bifunctional groups, the bifunctional groups preferably being selected from the substance group consisting of maleimide derivatives, alkyl halides, aryl halides, isocyanates, glutaraldehydes, acrylating reagents and imidoesters. By this means, the release of the molecular substance is in particular achieved in the lysosome, in the cytoplasmic space or in the nucleus.

It has proven to be particularly expedient that the bifunctional groups react with cysteine residues on the capsomere. It is additionally regarded as advantageous that the interacting structure comprises affinity-increasing groups such as 4-iodoacetamidosalicylic acid and/or p-arsonic acid phenyldiazonium fluoroborate and/or derivatives thereof. The structure can also be formed by epitopes-of the VP1 pentamer.

According to a further embodiment of the invention, a vehicle is provided where, using at least one further capsomere, it is possible to prepare a capsid-like structure for the transport of the molecular substance into a prespecified type of cells or to a prespecified site in the intracellular region. The further capsomere can be a capsomere according to the invention. The capsid-like structure, however, can also be prepared using further capsomeres not according to the invention. The choice of the type of capsomeres and their combination for the preparation of the capsid-like structure depends on the nature of the cell or on the prespecified location in the intracellular region, into which or to which the molecular substance is to be transported.

Expediently one side of the capsomere is part of the inside of the capsid-like structure, the capsid-like structure preferably being derived from the polyoma virus. Finally, the capsid-like structure can comprise at least one VP-2 and/or VP-3 protein.

For the preparation of a vehicle according to the invention, a process comprising the following steps is proposed:

i) synthesis, purification or isolation of the capsomere; and ii) complexation of the molecular substance using the capsomere.

A development of the process consists in modifying suitable residues of the capsomere, in particular its cysteine residues, with bifunctional groups after step i. The modification can expediently be carried out using one or more of the following substances: maleimide derivatives, alkyl halides, aryl halides, isocyanates, glutaraldehydes, acrylating reagents and imidoesters.

The vehicle according to the invention can preferably be used as a pharmaceutical carrier for the administration of molecules such as DNA, RNA, oligonucleotides, PNA, proteins, peptides and of low molecular weight lipophilic and lipophobic reagents, of colloidal gold, gold-labeled proteins and peptides to eukaryotic cells.

According to the invention, a combination of the vehicle according to the invention with agents suitable or necessary for the administration, for example reagents, solvents and the like, is furthermore proposed. A combination of agents for carrying out the process according to the invention is likewise proposed. This combination can also include apparatus and the like.

The invention is described in greater detail with the aid of the following examples and illustrations.

DETAILED DESCRIPTION OF THE PREFERRED EMBODIMENT

The following examples describe one possible embodiment of the invention.

1) Expression of the VP1 Protein of Polyoma Virus in *E.coli*

A gene of the VP1 coat protein of the murine polyoma virus is taken which contains sequence features of both the strain A2 and the strain A3. The coding sequence beginning with the ATG or the following amino acid is cloned immediately behind a factor Xa cleavage site in a derivative of the commercially available vector pQE 10 from Quiagen. This vector provides the fusion protein Xa cleavage site VP1 at the amino terminus with a histidine sequence. The fusion construction thus obtained is cloned inside a marker gene (lacZ complementation) and is inducible via the lacZ promoter. The final construction is transformed in *E. coli* cells suitable for the expression of pQE vectors. When the cells, after prior culture, are in the logarithmic phase, they are induced by addition of a suitable inductor, e.g. IPTG. After this, they express large amounts of a fusion protein containing the VP1 protein. The fusion protein is harvested after induction for 6 hours. It is present in soluble form and can be prepared pure on nickel chelate columns with minor changes to the purification protocol of Quiagen. By incubation with factor Xa, the pure VP1 protein portion of the fusion protein can be removed again from the nickel chelate column. The VP1 protein obtained is present in very pure form and forms pentamers by itself. The proteins VP2 and VP3 can be prepared analogously.

Figure 1:
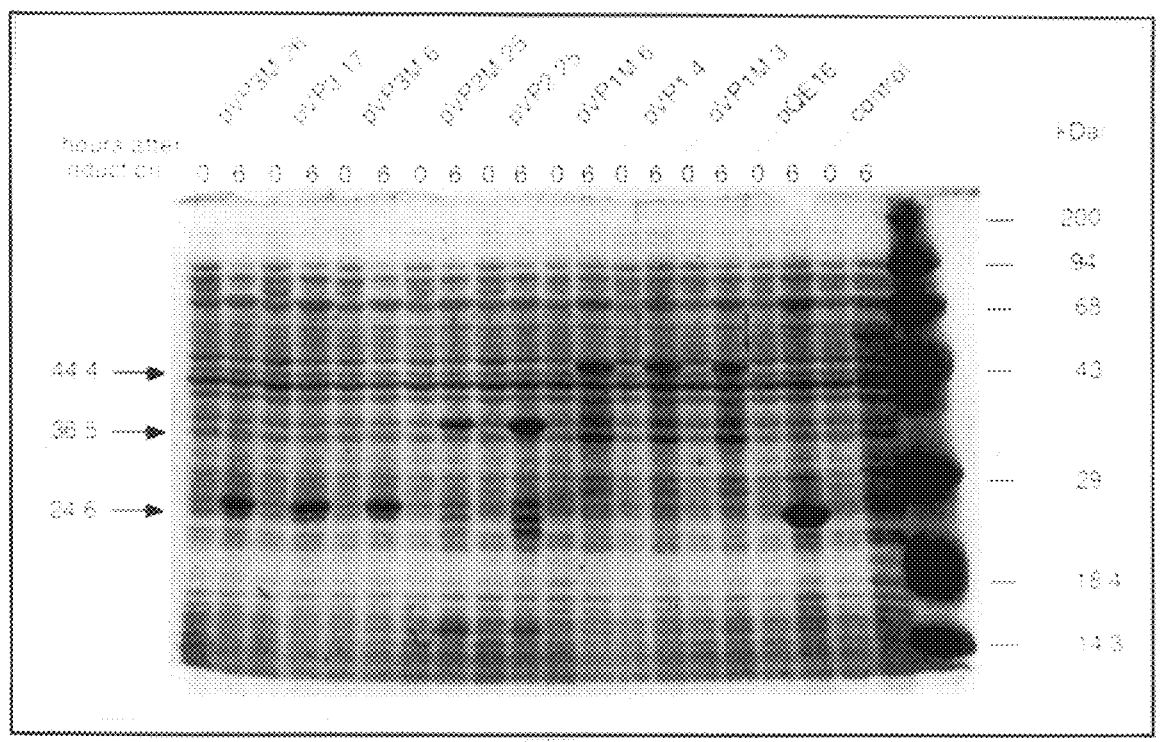
FIG. 1 shows the gel electrophoretic detection of VP3, VP2 and VP1 fusion proteins, FIG. 2 on the left shows an electron microscopic view of pentamers formed from the VP1 protein and on the right shows a computer-assisted illustration of the 5-fold symmetry of the pentamers.
Figure 2:
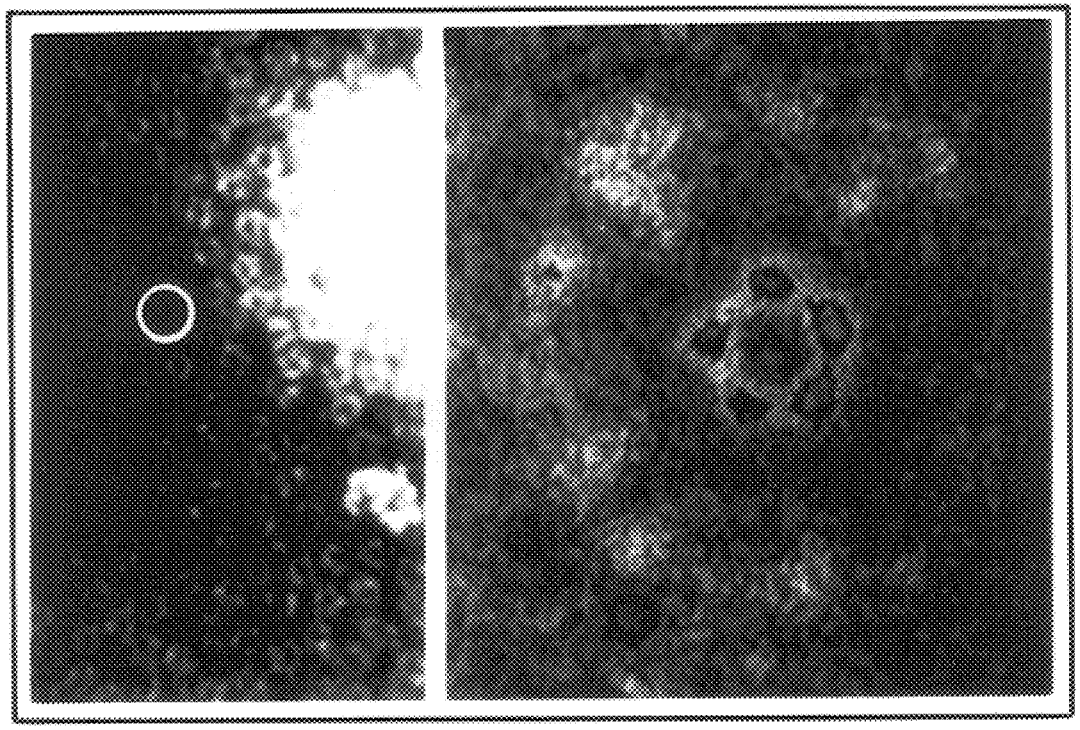

FIG. 1 shows the gel electrophoretic detection of the VP3, VP2 and VP1 fusion proteins. Shown in FIG. 2 are on the left an electron microscopic view of pentamers formed from the VP1 protein and on the right a computer-assisted illustration of the 5-fold symmetry of the pentamers.

2) Modification of the Cysteine Residues on One Side of the Pentamers before their Assembly The VP1 pentamers obtained according to example 1 above have a plurality of structures which can be converted into bifunctional groups by reaction with suitable reagents. The structures are found on the side of the pentamers which corresponds to its inside after assembly to give the capsid. The reagent used is a 3-maleimidobenzoyl-N-hydroxysuccinimide ester dispersed in an acetone/methanol/water mixture, which on one side of the reactive center carries as reactive groups SH groups and on the other side a reactive ester group, namely an amino group-reactive succinimide ester. The dispersion is mixed with the dissolved VP1 proteins so that a quantitative reaction takes place.

Shown in Table 1 are the loop structures of polyoma capsomeres which are to be found on one side of the capsomeres and which after assembly point to the inside of the capsid or the capsid-like structure:

Table 1

Loop 1: Asp 38, Leu 39, Val 40, Thr 41, Gly 42, Pro 43, Asp 44, Ser 45

Loop 2: Asn 109, Glu 110, Asp 111, Leu 112, Thr 113, Lys 114, Asp 115, Thr 116, Leu 117

Tail: N-terminus of amino acid residue 1 to residue 29 (at least from the amino acid 18 of the N-terminus which is well localized in the structural analysis up to residue 29): Lys 18, Ala 19, Cys 20, Pro 21, Arg 22, Pro 23, Ala 24, Pro 25, Val 26, Pro 27, Lys 28, Leu 29

Loop 3: Tyr 354, Asp 355, Gly 356, Thr 357, Gln 358, Pro 359, Val 360

3) The Assembly of VP1 Pentamers to give VP1 Capsids

Figure 3A:
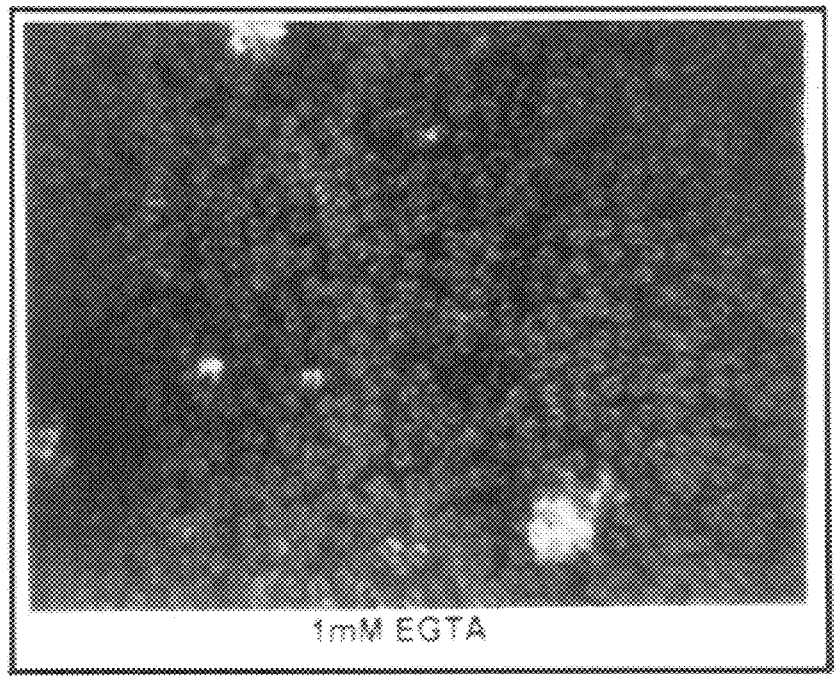
FIGS. 3A through 3C shows prepared pentamers and capsids formed therefrom.
Figure 3B:
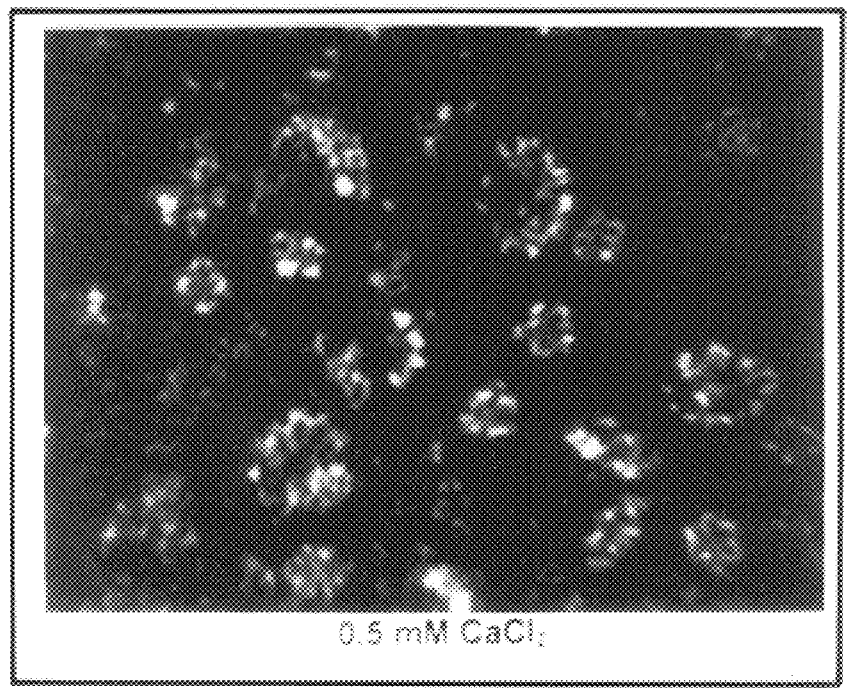
Figure 3C:
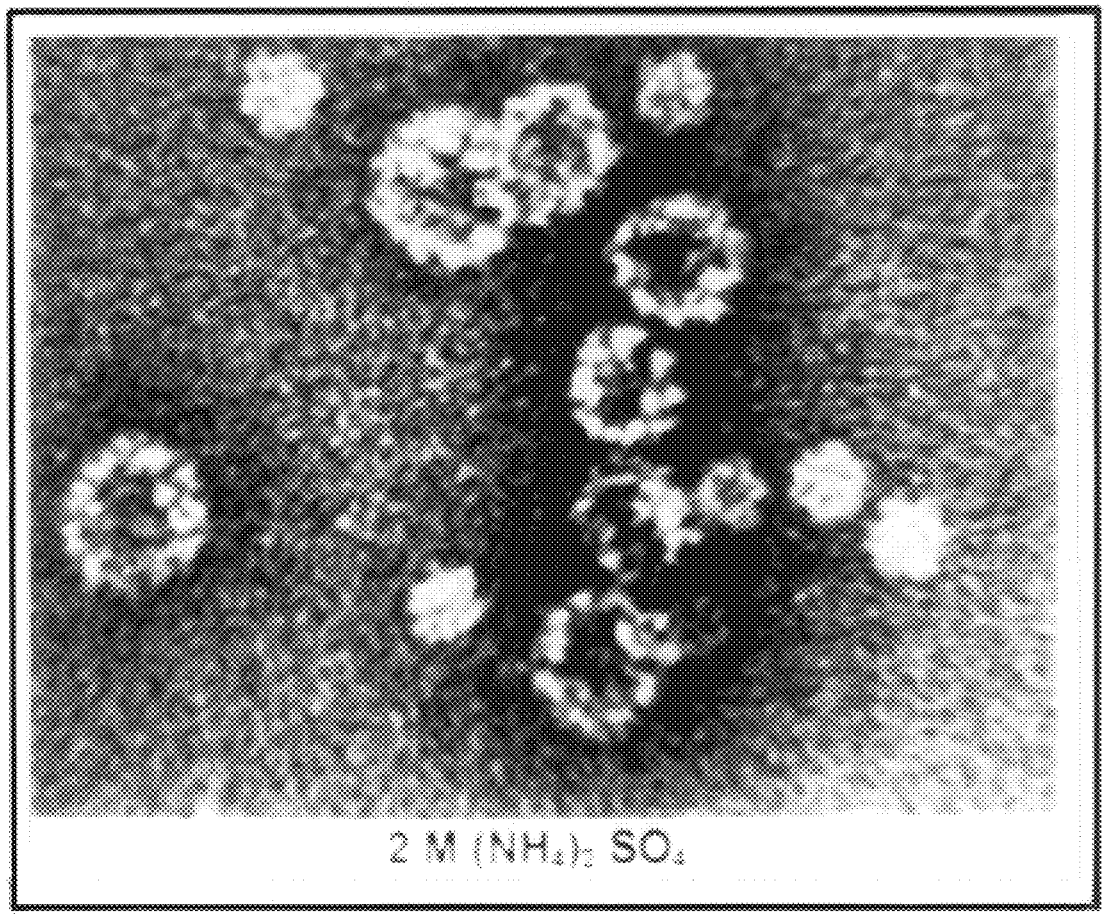

The VP1 pentamers are present in a buffer solution which contains EGTA to stabilize the pentameric non-assembled state. Magnesium ions, sodium ions and tris/HCl, pH 7.6, are further added to the buffer solution to stabilize the pH. The protein solution is transferred to a dialysis chamber and dialyzed against a 2M ammonium sulfate solution. After several changes of the dialysis buffer, the VP1 pentamers form capsids. These do not differ from empty capsids of the polyoma virus on inspection in the electron microscope, in diameter, or in their stability, although they lack the inner coat proteins VP2 and VP3. FIGS. 3A through 3C shows the pentamers prepared and capsids formed therefrom.

4) The Packing of DNA Oligonucleotides in Polyoma VP1 Capsids

Figure 4:
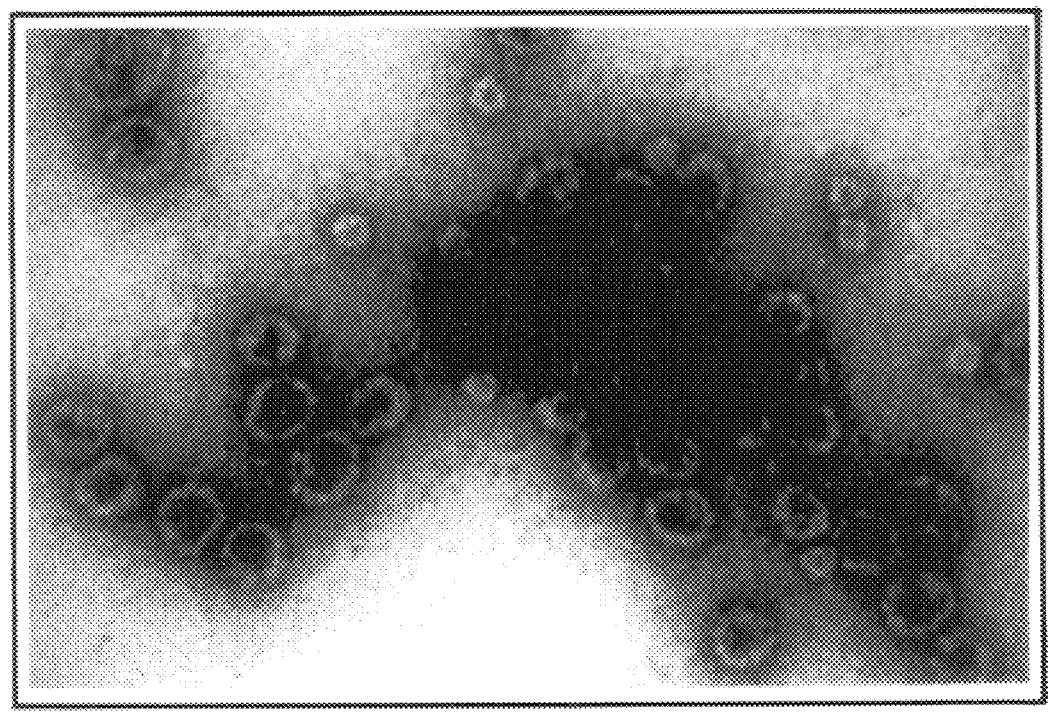
FIG. 4 shows an electron microscopic view of loaded VP1 capsids.

Conventional oligonucleotides, i.e. those unchanged in their chemical structure, can be packed into polyoma VP1 capsids in high yield according to the following protocol: capsid structures, such as have been obtained in Example 3, are buffered to pH 5.5. They are then reacted in an osmotic shock procedure with an equi- or higher molar amount, typically with a two-fold molar excess, of oligonucleotides. For the oligonucleotides used in this example (20-mers) a weight ratio of about 1:6 thus results compared with the VP1 protein. The form of the VP1 capsids loaded with oligonucleotides thus obtained cannot be differentiated in the electron microscope from the unloaded VP1 capsids. FIG. 4 shows an electron microscopic view of loaded VP1 capsids.

What is claimed is:

1. A process for the preparation of a vehicle with molecular substance selected from the group consisting of DNA, RNA, protein, PNA, lipophilic pharmaceuticals and lipophilic pharmaceuticals for transport into eukaryotic cells, comprising at least one capsomere formed, developed or originating from an animal or plant virus, which capsomere is formed such that it is suitable for the construction of a capsid and on one of its sides has a structure interacting with the molecular substance such that the molecular substance can be bound or added to the capsomere, and where the one side of the capsomere after assembly is a constituent of the inside of the capsid, comprising the following steps:

i) synthesis, purification or isolation of the capsomere and
  ii) complexation of the molecular substance using the capsomere.

2. The process as claimed in claim 1, where the capsomere is formed or developed from the polyoma virus.

3. The process as claimed in claim 2, where the capsomere is formed from the VP1 pentamer of the polyoma virus or is formed or developed therefrom.

4. The process as claimed in claim 1, where the capsomere is obtained from "non-enveloped" viruses selected from the group consisting of DNA-containing Papovaviridae, optionally polyoma and papilloma viruses, Iridoviridae, Adenoviridae and Parvoviridae or selected from the group consisting of RNA-containing Picornaviridae, optionally polio viruses, Caliciviridae, Reoviridae and Cirnaviridae or is formed or developed therefrom.

5. The process as claimed in claim 1, where the capsomere is obtained from the outer and/or inner coat of "enveloped" viruses selected from the group consisting of DNA-containing Poxviridae, Herpesviridae and Hepadnaviridae or selected from the group consisting of RNA-containing Retroviridae, Paramyxoviridae, Sendai viruses, Orthomyxoviridae, Bunyaviridae, Arenaviridae, Toroviridae, Togaviridae, Flaviviridae, Rhabdoviridae and Filoviridae or is formed or developed therefrom.

6. The process as claimed in claim 1, where the structure interacts with the molecular substance via lipophilic interactions and/or bonds based on covalent bonds, ionic bonds or hydrogen bridges.

7. The process as claimed in claim 6, where the structure is selected from the group consisting of a maleimide moiety, alkyl halides, aryl halides, isocyanates, glutaraldehydes, acrylating reagents and imidoesters.

8. The process as claimed in claim 7, where the structure reacts with cysteine residues on the capsomere.

9. The process of claim 6, where the structure is selected from the group consisting of 4-iodoacetamidosalicylic acid, p-arsonic acid phenyldiazonium fluroborate and compounds obtained thereof.

10. The process of claim 1, where the structure is formed by epitopes of the VP1 pentamer.

11. The process as claimed in claim 1, where after step i cysteine residues of the capsomere are modified with a bifunctional reagent.

12. The process as claimed in claim 11, where the bifunctional reagent is selected from the group consisting of a maleimide moiety, alkyl halides, aryl halides, isocyanates, glutaraldehydes, acrylating reagents and imidoesters.

13. The product of the process of claim 1.

14. The process of claim 1 where at least one additional capsomere is used to prepare the capsid.

15. The process of claim 1 or claim 14, where the capsid comprises at least one VP-2 and/or VP-3 protein.

* * * * *

UNITED STATES PATENT AND TRADEMARK OFFICE
CERTIFICATE OF CORRECTION

PATENT NO. : 6,165,772
DATED : December 26, 2000
INVENTOR(S) : Bertling

It is certified that error appears in the above-identified patent and that said Letters Patent is hereby corrected as shown below:

Column 2,
Line 38, delete the hyphen "-".

Column 4,
Line 65, delete "philic" and insert -- phobic --.

Signed and Sealed this

Eleventh Day of December, 2001

*Attest:*

NICHOLAS P. GODICI
*Attesting Officer*   *Acting Director of the United States Patent and Trademark Office*